United States Patent [19]

Chan

[11] Patent Number: Plant 5,710

[45] Date of Patent: Apr. 8, 1986

[54] PEACH TREE

[76] Inventor: Ronald L. Chan, 506 Ohleyer Rd., Yuba City, Calif. 95991

[21] Appl. No.: 675,319

[22] Filed: Nov. 26, 1984

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is large, vigorous, upright, dense, vase form, and hardy; foliated with medium size, lanceolate, acutely pointed leaves having a crenate margin, short thick petiole, and alternate, globose, red glands; blooms early from hardy, medium size, medium length, pointed, appressed, pubescent flower buds; the flowers being of medium size and pink; and is a regular and very productive bearer of early ripening, medium but variable size, clingstone fruit of symmetrical, globose form; the fruit having yellow skin partially overspread with red, and yellow flesh.

1 Drawing Figure

BACKGROUND OF THE VARIETY

1. Field of the Invention

As an owner of a ranch, including orchards, located near Yuba City, Sutter County, Calif., I frequent such ranch and orchards for the purpose of inspection, and the supervision of soil cultivation, irrigation, and harvesting of crops. Against this background of my activities, the present variety of peach tree was discovered by me.

2. Classification of the Variety

The present variety of peach tree is embraced by Class 43, Plants, of the United States Patent Office MANUAL OF CLASSIFICATION.

3. Prior Varities

Among existing varieties of peach trees which are known to me and mentioned herein, are the Andross, Fortuna, and Loadel; all unpatented.

ORIGIN OF THE VARIETY

The present variety of peach tree was discovered by me growing as a full-scaffold, sport limb on an Andross peach tree in an orchard located as aforesaid; it having been observed by me that such sport limb bore fruit having an earlier ripening period than the remainder of the fruit on the host tree. Such sport limb was—after my discovery of it—maintained under close and continuing observation in order to confirm such earlier ripening period of its fruit, and other characteristics which I recognized. Upon such confirmation, I determined to asexually reproduce the present variety of peach tree in contemplation of its potential for commercial growing.

ASEXUAL REPRODUCTION OF THE VARIETY

The present variety of peach tree was asexually reproduced, on my behalf, by budding undertaken by a commercial nursery, and the reproductions—grown on the aforesaid ranch—ran true, in maturity, in all respects.

SUMMARY OF THE VARIETY

The present variety of peach tree is large, vigorous, upright, dense, vase form, and hardy; foliated with medium size, lanceolate, acutely pointed leaves having a crenate margin, short thick petiole, and alternate, globose, red glands; blooms early from hardy, medium size, medium length, pointed, appressed, pubescent flower buds; the flowers being of medium size and pink; and is a regular and very productive bearer of early ripening, medium but variable size, clingstone fruit of symmetrical, globose form; the fruit having yellow skin partially overspread with red, and yellow flesh.

The present variety of peach tree is further and more particularly characterized as follows:

The fruit ripens about six days before other comparative, early ripening, clingstone peach varieties such as the Andross, Fortuna, and Loadel; this being of substantial advantage in that it permits acceleration by several days of the commercial canning season.

Additionally, the fruit—which keeps well and is of excellent canning quality and high flavor—sizes better than other comparative, early-ripening, clingstone peach varieties, and of which the Loadel is representative; and has a large fruit/pit ratio, and a lack of split pits and gumming.

The tree is more vigorous in growth and has a higher percentage of fruit set than other comparative, early-ripening, clingstone peach varieties.

BRIEF DESCRIPTION OF THE DRAWING

The drawing is an illustration, by photographic reproduction in color, of a twig with leaves and fruit, and separate fruit; one of the latter being partially cut away to expose the flesh.

DESCRIPTION OF THE VARIETY

The botanical details of this new and distinct variety of peach tree—with color definitions (except those in common color terms) referenced to Maerz and Paul Dictionary of Color—are as follows:

Tree:

*Size.*—Large.
*Vigor.*—Vigorous.
*Growth.*—Upright.
*Density.*—Dense.
*Form.*—Vase-formed.
*Hardiness.*—Hardy.
*Production.*—Very productive.
*Bearing.*—Regular bearer.

Trunk

*Size.*—Medium.

*Texture.*—Shaggy.

Branches:

*Size.*—Medium.

*Texture.*—Medium.

*Color.*—Brown.

Lenticels:

*Number.*—Numerous.

*Size.*—Medium.

Leaves:

*Size.*—Medium. Average length — 5". Average width — $1\frac{1}{4}$".

*Form.*—Lanceolate. Acutely pointed.

*Thickness.*—Thin.

*Color.*—Top side — Dark green (23-L-9). Under side — Lighter green (22-J-6).

*Texture.*—Smooth.

*Margin.*—Crenate.

*Petiole.*—Short. Thick.

*Glands.*—Average number — 2 per leaf. Alternate. Small. Globose. Red. Positioned on petiole and base of blade.

*Stipules.*—Wanting.

Flower buds:

*Hardiness.*—Hardy.

*Size.*—Medium.

*Length.*—Medium.

*Form.*—Pointed. Appressed.

*Pubescence.*—Pubescent.

Flowers:

*Blooming period.*—Date of first bloom — February 23rd. Date of full bloom — March 8th. Early, as compared to other varieties.

*Size.*—Medium.

*Color.*—Pink.

Fruit:

*Maturity when described.*—Hard ripe — July 15th.

*Date of picking.*—July 10th–July 15th.

*Size.*—Medium but variable. Average diameter axially — $2\frac{1}{2}$". Average transversely in suture plane — $2\frac{1}{2}$".

*Form.*—Symmetrical. Globose.

*Suture.*—Distinct. Shallow.

*Ventral surface.*—Rounded strongly.

*Base.*—Truncate.

*Apex.*—Short.

*Pistil point.*—Oblique.

Skin:

*Thickness.*—Medium.

*Texture.*—Medium.

*Tenacity.*—Tenacious to flesh.

*Tendency to crack.*—None.

*Color.*—Yellow (11-L-5) partially overspread with red (5-L-5). Somewhat streaked and mottled.

*Down.*—Moderate. Short.

Flesh:

*Color.*—Yellow (10-L-6). Surface of pit cavity — Yellow.

*Juice.*—Abundant.

*Texture.*—Firm. Crisp.

*Fibers.*—Fine.

*Ripens.*—Evenly.

*Flavor.*—Sweet.

*Aroma.*—Distinct.

*Eating quality.*—Good.

Stone:

*Type.*—Cling. Adheres to flesh over entire surface.

*Size.*—Small. Average length — $1\frac{7}{8}$". Average breadth — 1". Average thickness — 11/16".

*Form.*—Oval.

*Base.*—Straight.

*Hilum.*—Narrow.

*Apex.*—Acute.

*Sides.*—Equal.

*Surface.*—Furrowed throughout.

*Ridges.*—Rounded toward base.

*Pits.*—Elongated.

*Ventral edge.*—Thin.

*Dorsal edge.*—Full, with broad groove.

*Color.*—Brown (11-J-12).

*Tendency to split.*—Slight.

Use: Canning.

Keeping quality: Good.

Resistance to insects and diseases: Medium.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, particularly characterized by clingstone fruit which ripens about six days before the fruit of other comparative, early ripening, clingstone peach varieties and of which the Loadel is representative.

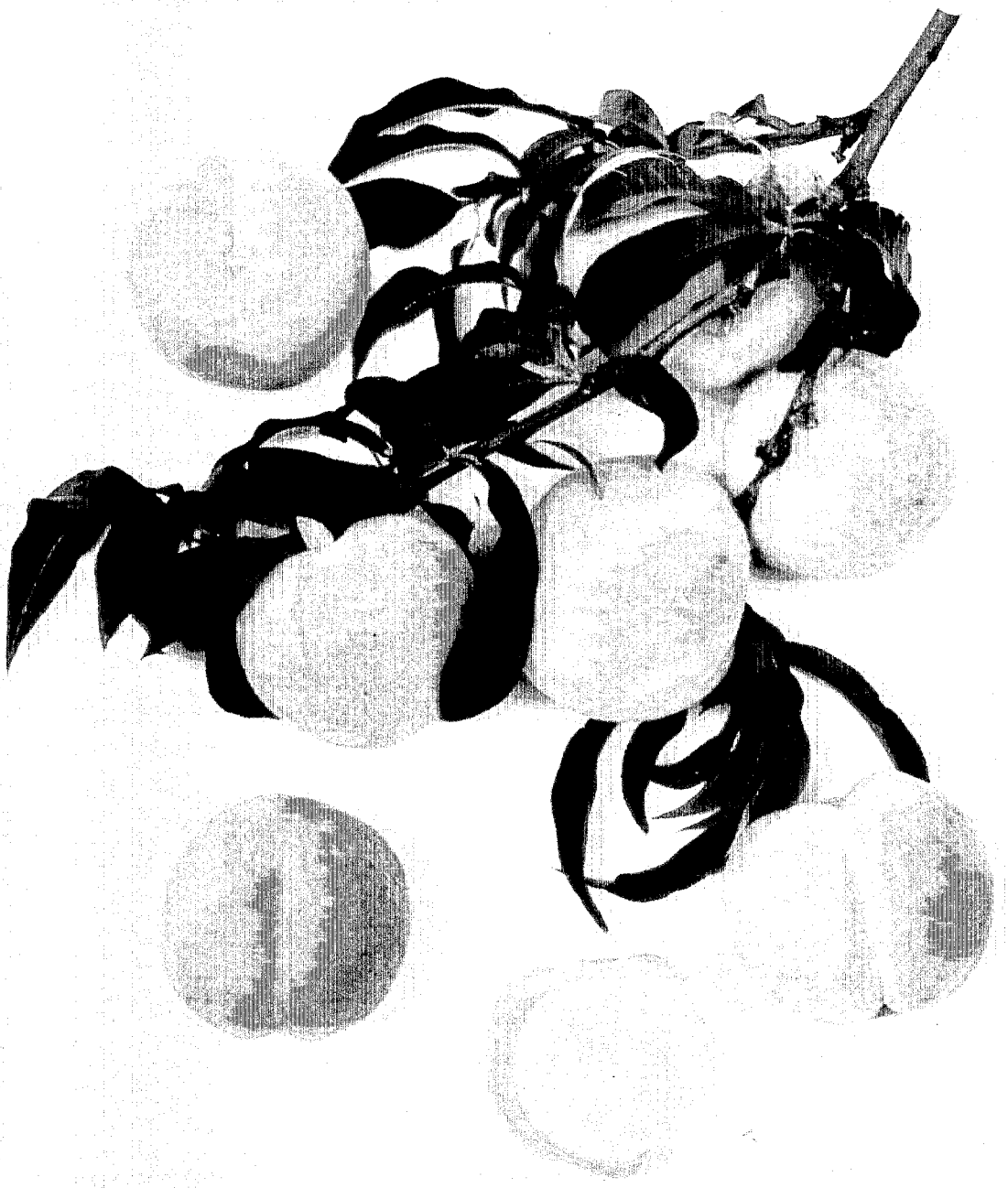

* * * * *